(12) United States Patent
Nordin

(10) Patent No.: US 7,318,726 B2
(45) Date of Patent: Jan. 15, 2008

(54) TOOTH ROOT CANAL POINT

(76) Inventor: Harald E. Nordin, Villa Amphion, Chemin du Chabloz 8, CH-1822, Chernex (CH)

( * ) Notice: Subject to any disclaimer, the term of this patent is extended or adjusted under 35 U.S.C. 154(b) by 0 days.

(21) Appl. No.: 11/184,090

(22) Filed: Jul. 19, 2005

(65) Prior Publication Data

US 2006/0024645 A1 Feb. 2, 2006

(30) Foreign Application Priority Data

Jul. 28, 2004 (EP) .................................. 04405479

(51) Int. Cl.
*A61C 5/04* (2006.01)
*A61C 13/30* (2006.01)

(52) U.S. Cl. .................................................. 433/224

(58) Field of Classification Search ................ 433/224, 433/220, 225
See application file for complete search history.

(56) References Cited

U.S. PATENT DOCUMENTS

| | | | | | |
|---|---|---|---|---|---|
| 674,419 | A | * | 5/1901 | Kinsman | .................... 433/224 |
| 1,463,963 | A | * | 8/1923 | Miller | ........................ 433/224 |
| 1,469,992 | A | * | 10/1923 | Card | ........................... 433/81 |
| 1,757,595 | A | * | 5/1930 | Siegel | ........................ 433/224 |
| 3,066,112 | A | * | 11/1962 | Bowen | ....................... 523/116 |
| 3,318,000 | A | * | 5/1967 | Paris | .......................... 433/224 |
| 4,525,147 | A | | 6/1985 | Pitz et al. | .................... 433/224 |
| 5,328,372 | A | | 7/1994 | Reynaud et al. | ............ 433/220 |
| 5,564,929 | A | | 10/1996 | Alpert | ........................ 433/224 |
| 6,267,597 | B1 | * | 7/2001 | Kim | .......................... 433/224 |
| 6,371,763 | B1 | | 4/2002 | Sicurelli, Jr. et al. | ........ 433/220 |

* cited by examiner

*Primary Examiner*—Ralph A. Lewis
(74) *Attorney, Agent, or Firm*—Ostrolenk, Faber, Gerb & Soffen, LLP

(57) ABSTRACT

The tooth root canal point is made of a synthetic material reinforced with glass or carbon fibers and not of the usual gutta percha. When inserted with bone cement, the result is a solid but not completely rigid post that conforms to the contours of the tooth root canal and ensures a high stability of the tooth.

7 Claims, 1 Drawing Sheet

TOOTH ROOT CANAL POINT

REFERENCE TO RELATED APPLICATION

This application claims the benefit of the filing date of European Patent Application No. 04405479.9 filed 28 Jul. 2004, the disclosure of which is hereby incorporated by reference.

FIELD OF THE INVENTION

The present invention relates to a tooth root canal point for filling the tooth root canal following a root canal treatment. According to the prior art, this is mainly achieved by means of tooth root canal points of gutta percha, i.e. of a material that is flexible enough to conform to the bends of a tooth root canal. Beforehand, the tooth root canal is prepared and shaped by means of drills and files, and then the gutta percha point is heated and inserted. Both the files and the points are mutually standardized. The heating gives the gutta percha a limited ability to penetrate into dentine cracks and fine canals.

Furthermore, tooth root canal points of paper and for temporary treatments of calcium hydroxide are known in the art.

BACKGROUND OF THE INVENTION

A flexible, rope-like dental prosthesis is known from U.S. Pat. No. 5,564,929, the rope consisting of glass, ceramic, carbon or other fibers. The rope is treated with a stiffening agent and inserted in the tooth root canal where it stiffens.

U.S. Pat. No. 4,525,147 discloses a tooth root canal implant containing carbon fibers, thereby allowing to perform a measurement of the electrical conductivity for measuring the proximity of the implant to the apical end of the canal.

All tooth root canal points have in common that they are not very strong and are therefore only capable of filling out the tooth root canal but incapable of strengthening the tooth that is weakened due to the removal of the pulp.

On the background of this prior art, it is the object of the present invention to provide a tooth root canal point that confers the tooth increased stability. This object is attained by the tooth root canal point made of a fiber-reinforced synthetic material.

BRIEF DESCRIPTION OF THE DRAWING

The invention will be explained in more detail hereinafter with reference to a drawing of an exemplary embodiment where single

DESCRIPTION OF PREFERRED EMBODIMENTS OF THE INVENTION

Figure 1:
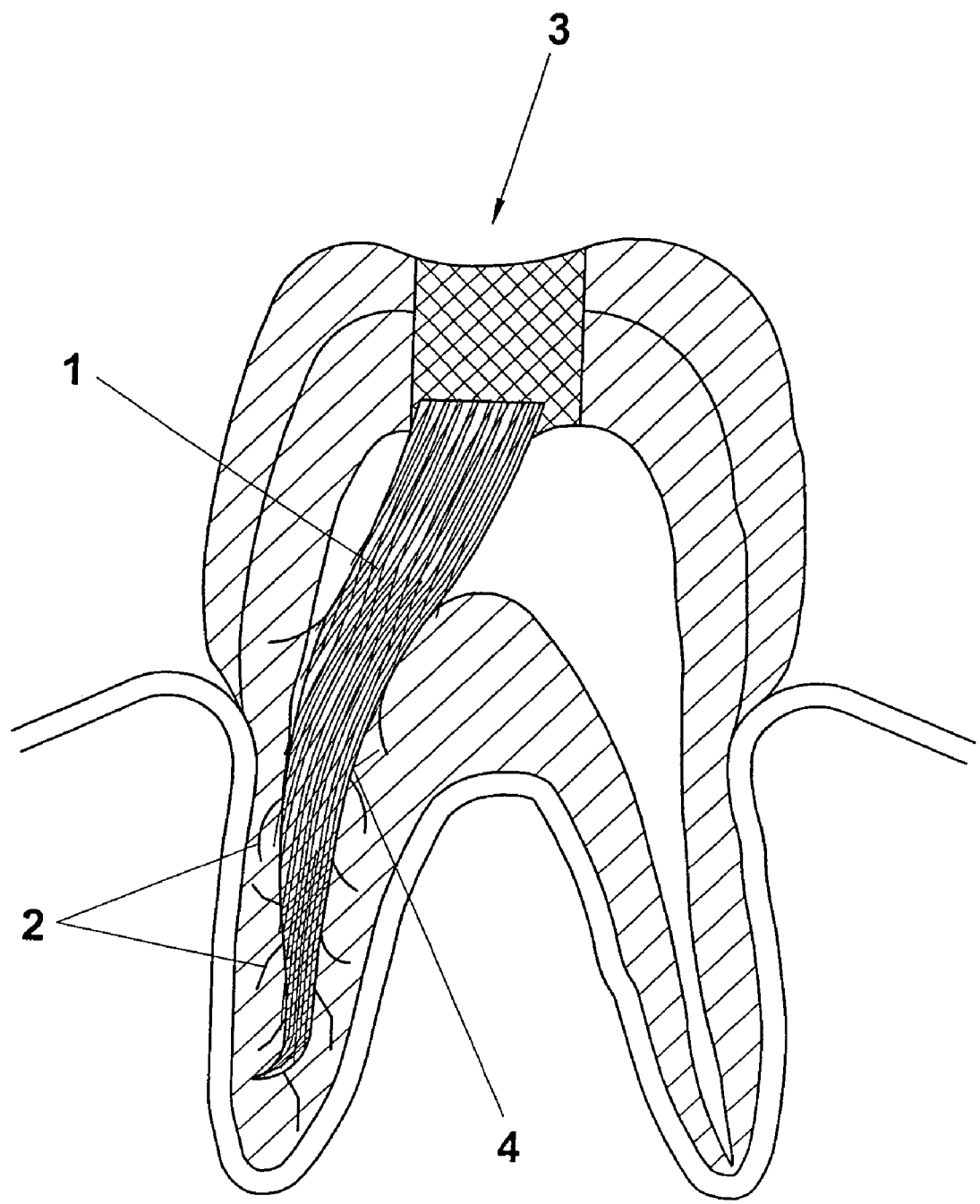

FIG. 1 schematically shows a sectional view of a tooth root canal point of the invention in a tooth, and specifically, shows by way of example, an application in which the point is entirely enclosed within the tooth.

Tooth root canal point 1 is made of a fiber-reinforced synthetic material wherein the fibers may be glass, carbon, or ceramic fibers 2. The fibers are preferably arranged in parallel to each other approximately and are held together by means of a suitable synthetic material or resin, respectively, but only to such an extent that a required degree of flexibility is still ensured and that fibers or fiber strands may penetrate in lateral cracks or the like in root canal 4 of tooth 3. It is apparent in the FIGURE that the root canal post is able to follow the curved root canal.

For a better adhesion of the fibers to the synthetic resin, they are coated with a suitable synthetic layer, e.g. with a layer of vinyl silane. In principle, the points of the invention should correspond to the same standard norms as the gutta percha points, however with somewhat reduced dimensions to take account of the cement.

The point is inserted using a bone cement, thereby stiffening the fiber-reinforced tooth root canal point after the cement has hardened and thus conferring the tooth a substantially higher strength as compared to tooth root canal points of the prior art. By a corresponding choice of the individual components, i.e. of the point and the cement, it is achieved that the resulting modulus of elasticity is approximately equal to that of the tooth.

The insertion of the points of the invention takes place in the same way as that of the points of the prior art and therefore requires neither new instruments nor new techniques.

What is claimed is:

1. A tooth root canal point made of a fiber-reinforced synthetic material, the point comprising:
    a bundle of fibers configured to be inserted into a root canal such that fibers of the bundle of fibers extend lengthwise along a length of the root canal, the fibers of the bundle of fibers comprising a distal end length, the distal end length being an extent at a lengthwise distal end of the fibers,
    wherein the bundle of fibers is held together to enable one or more of the fibers or fiber strands of the bundle to separate along the distal end length thereof from the bundle of fibers, such that the separated distal end length protrudes away from the bundle of fibers to penetrate one or more openings in a lateral wall of the root canal.

2. The tooth root canal point according to claim 1, wherein the point is comprised of fibers arranged substantially parallel to each other and coated with the synthetic material.

3. The tooth root canal point according to claim 1, wherein the fibers are glass fibers.

4. The tooth root canal point according to claim 1, wherein the point is affixed with a bone cement into the tooth root canal, wherein the tooth root canal point and the cement exhibit approximately the same modulus of elasticity as the tooth.

5. The tooth root canal point of claim 2, wherein the synthetic material is vinyl silane embedded in a synthetic resin.

6. The tooth root canal point of claim 1, wherein the point is of a length adapted for being entirely enclosed within a tooth.

7. A tooth root canal point made of a fiber-reinforced synthetic material, the point comprising:
    a bundle of fibers configured to be inserted into a root canal such that fibers of the bundle of fibers extend lengthwise along a length of the root canal, the fibers of the bundle of fibers comprising a distal end length, the distal end length being an extent at a lengthwise distal end of the fibers,
    wherein the bundle of fibers is held together to enable one or more of the fibers or fiber strands of the bundle to separate along the distal end length thereof from the bundle of fibers, such that the separated distal length protrudes away from the bundle of fibers to penetrate one or more openings in a lateral wall of a root canal, and
    the bundle of fibers having a modulus of elasticity approximately equal to the modulus of elasticity of the tooth.

* * * * *